(12) United States Patent  (10) Patent No.: US 8,097,016 B2
Djurovic  (45) Date of Patent: Jan. 17, 2012

(54) DIRECTLY INSERTABLE LAPAROSCOPIC CLOSURE DEVICE, HEMOSTASIS AND DRAIN

(76) Inventor: Zarija Djurovic, Chicago, IL (US)

( * ) Notice: Subject to any disclaimer, the term of this patent is extended or adjusted under 35 U.S.C. 154(b) by 230 days.

(21) Appl. No.: 12/604,261

(22) Filed: Oct. 22, 2009

(65) Prior Publication Data

US 2011/0098681 A1    Apr. 28, 2011

(51) Int. Cl.
*A61B 17/08* (2006.01)
*A61D 1/00* (2006.01)
*A61F 5/44* (2006.01)

(52) U.S. Cl. ............ 606/213; 604/332; 604/337

(58) Field of Classification Search ........... 604/337, 604/338, 343; 606/213, 216, 217
See application file for complete search history.

(56) References Cited

U.S. PATENT DOCUMENTS

2002/0095160 A1*   7/2002   Bonutti .............. 606/119

* cited by examiner

*Primary Examiner* — Melanie Hand
(74) *Attorney, Agent, or Firm* — Clifford Kraft

(57) ABSTRACT

A laparoscopic surgery close device used to close an entrance hole into a patient's abdomen with other embodiments that can function as a hemostasis device or as a drain device. An elongated stem with christmas-tree serrations (one way) has an inflatable balloon on a distal end and an anchor disk that can slide over the stem from the proximal end. After inserting the stem into a surgical entrance hole in a patient's abdomen, the balloon can be inflated providing support from the bottom, and the anchor disk can be slid on from the top effectively pinching the tissue along the hole. The device can be left in for around 5-6 days to allow healing to take place. After that, the balloon can be deflated, and the device can be pulled out. A second embodiment has a lager diameter hollow stem and can be used as a hemostasis device where the surgeon can pinch off a bleeding blood vessel and continue surgery through the same entrance port. A third embodiment is longer with slightly larger diameter hollow stem and can be used as a drain. An alternate embodiment uses a soft tube as a stem with a split disk anchor that pinches it when engaged.

20 Claims, 8 Drawing Sheets

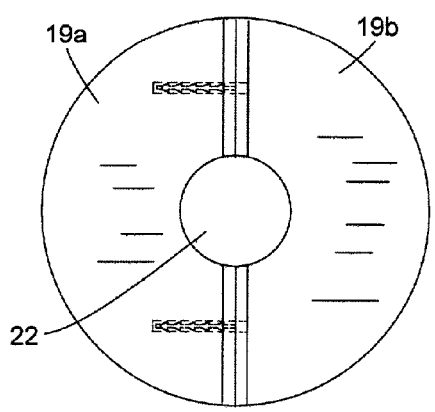 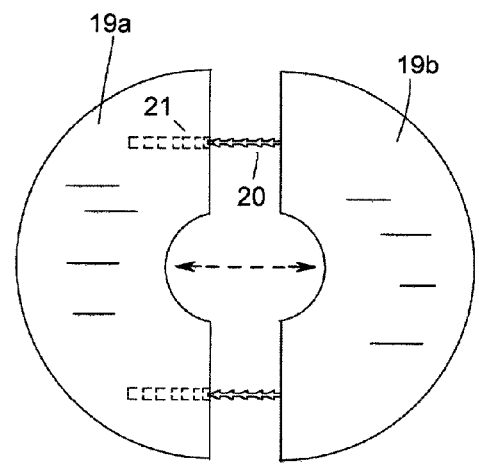
FIG. 7A  FIG. 7B

DIRECTLY INSERTABLE LAPAROSCOPIC CLOSURE DEVICE, HEMOSTASIS AND DRAIN

FIELD OF THE INVENTION

The present invention relates generally to laparoscopic or minimally invasive surgery and more particularly to an insertable device that, in different embodiments, can be used as a port close, a hemostasis device and a drain.

DESCRIPTION OF THE PRIOR ART

Laparoscopic surgery is usually performed on the abdomen using a very small (0.5-1.5 cm) incision (port). The depth of the port may be from 1-3 inches depending on the patient. A device called a laparoscope is inserted into the opening and used to perform surgery within the abdominal wall. The laparoscope generally includes some type of imaging system as well as the ability to perform different functions required during surgery. In preparation for laparoscopic surgery, the patient's abdomen is usually insufflated with a relatively inert gas such as carbon dioxide.

After the surgery is complete, the surgeon must close the hole in the abdominal wall. This hole penetrates through the skin, fascia (a fatty fibrous layer), muscle and peritoneum (membrane that forms the lining of the abdominal cavity). Using prior art techniques, the surgeon usually sutures or sews the hole from the outside. This has the disadvantage of not completely pulling the various layers tightly into position where they can heal (as stated, the hole may be from 1-3 inches long). Even though the hole is relatively small in diameter, incomplete healing, re-opening and infection are constant problems because of insufficient closing in the lower part of the hole.

It would be advantageous to have a device that could be inserted through the hole from the outside that would draw the various layers together and hold them for the several days needed for healing (5-6 days). Removing the device should be a simple outpatient procedure.

Also during laparoscopic surgery, occasionally the surgeon will cut into a small blood vessel while making the insertion hole in the abdominal wall. This blood vessel will bleed causing several difficulties for the surgeon. First, the surgeon must stop the bleeding. This usually requires an enlargement of the hole. Second, bleeding in or around the hole makes it difficult to proceed. Generally when this happens, the surgeon must abandon that hole and make another (with a very real chance of the same thing happening again). It would be advantageous to have a hemostasis device that could be inserted through the hole that would lock in the hole making the hole large enough for the surgeon to stop the bleeding and to then proceed with the surgery using that same hole. This device could have a very similar structure to the closing device described above but with a larger diameter.

Finally, it would be advantageous to have a similar device that could temporarily lock in the hole and provide a fluid drain where excess fluids could be removed.

SUMMARY OF THE INVENTION

The present invention relates to a laparoscopic surgery close device used to close an entrance port into a patient's abdomen with other embodiments that can function as a hemostasis device or as a drain device. An elongated stem with christmas-tree serrations (one way) has an inflatable balloon on a distal end and an anchor disk that can slide over the stem from the proximal end. After inserting the stem into a surgical entrance hole in a patient's abdomen, the balloon can be inflated (usually with liquid) providing support from the bottom, and the anchor disk can be slid on from the top effectively pinching the tissue along the hole. The device can be left in for around 5-6 days to allow healing to take place. After that, the balloon can be deflated, and the device can be pulled out. A second embodiment has a lager diameter hollow stem and can be used as a hemostasis device where the surgeon can pinch off a bleeding blood vessel and continue surgery through the same entrance port. A third embodiment is longer with slightly larger diameter hollow stem and can be used as a drain.

In an alternate embodiment, a split disk can squeeze down on the stem which can be a soft tubing.

DESCRIPTION OF THE FIGURES

Attention is now directed at several drawings that illustrate features of the present invention:

FIGS. 7A-7B shows details of the split disk of the embodiment of FIG. 6.

Several drawings and illustrations have been presented to aid in understanding the features of the present invention. The scope of the present invention is not limited to what is shown in the figures.

DESCRIPTION OF THE INVENTION

The present invention relates to an insertable device that can be used in different embodiments as a laparoscopic port close or holding device, hemostasis device or drain. The present invention also includes the method of use of these devices. The device includes an elongated closed stem or tube that has christmas-tree serrations along its length. These serrations are merely ridges that extend outward from the stem and totally or partially encircle it that are formed to be flat on their bottom side inclined on their top side. This allows an anchor disk to be slid (clicked) downward along the stem from serration to serration, but not retracted upward (a one-way anchor). The anchor disk can be constructed so that it makes positive attachment to two serrations rather than only one for positive locking. At the bottom end of the stem, a balloon can be attached that can be inflated or deflated by a small inflation tube that runs through or along the stem. To use the present invention, the stem is inserted into the patient's abdomen through the hole along with the balloon. The balloon can then be inflated to give support on the bottom of the device. The surgeon can then slide the anchor disk along the serrations using a tool to hold the stem, so that the abdominal wall is pinched between the balloon and the anchor disk. Different embodiments of the present invention using different sized stems and tubes can be used not only as such a close, but also as a hemostasis device holding the hole stable so that the surgeon can repair the bleeding and then continue with the surgery through the same hole, and as a drain tube. The device can be easily removed by simply deflating the balloon and pulling it out.

An alternate embodiment uses a split disk that squeezes a soft tube stem.

Figure 1:
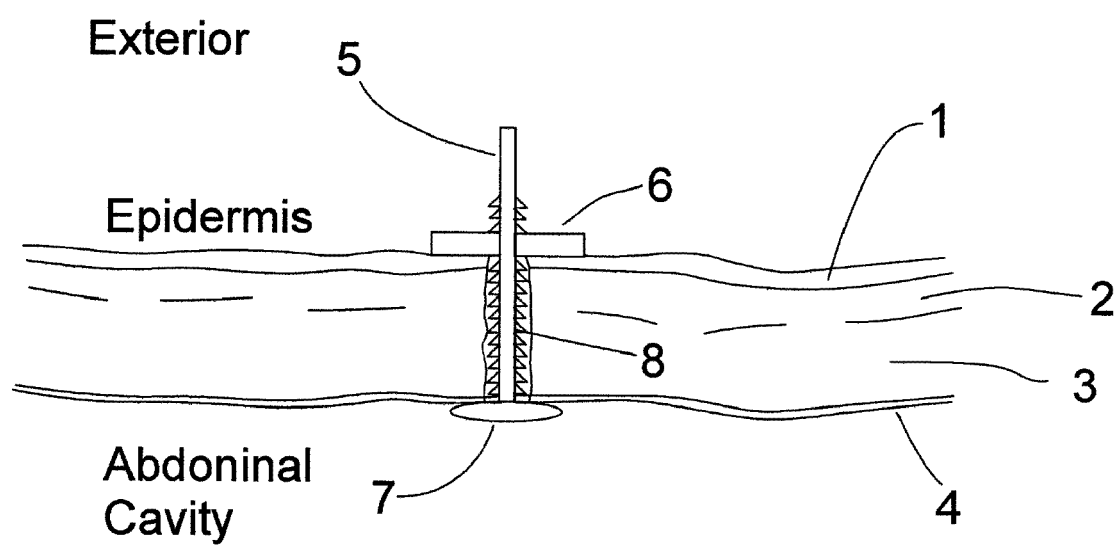
FIG. 1 shows a side sectional view of the abdominal wall with an embodiment of the present invention inserted for suturing.

FIG. 1 shows a side sectional view of the abdominal wall showing the skin 1, fascia 2, muscle 3 and peritoneum 4 with an embodiment of the device of the present invention inserted. The stem 5 contains christmas-tree serrations 8 that are gripped by the anchor disk 6. The abdominal wall is pinched between the anchor disk 6 and the inflated balloon 7. This locks the tissue in place top and bottom for healing. The outside diameter of the stem 5 can be around 2 to 5 mm. While this is the preferred diameter, considerable variation of the diameter is within the scope of the present invention. The diameter of the anchor disk 6 can be around 3 cm. The balloon diameter can also be around 3 cm. Again, this a preferred size; any size anchor disk or balloon is within the scope of the present invention.

Figure 2A:
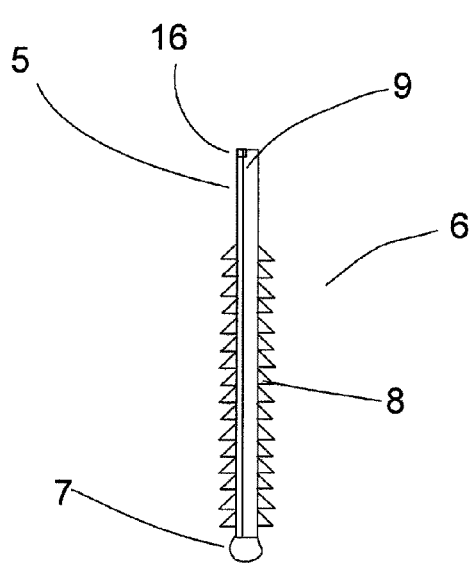
FIG. 2A shows a side view of the device of FIG. 1 before insertion.

FIG. 2A shows a side sectional view of the device of FIG. 1. The christmas-tree serrations 8 can be clearly seen running along a length of the stem 5. An inflation tube 9 can be seen running inside of the stem 5. In alternate embodiments, this tube 9 can run along the outside of the stem. A small valve 16 can be provided at the proximal end of the inflation tube 9. This inflation tube has liquid or gas communication with the balloon 7 that is located near the base of the stem 5. In some embodiments, the balloon 7 can fit over the stem like a collar or doughnut. The valve 16 only needs to be a plug of silicone. The surgeon can pass a needle through the valve 16 in order to inflate or deflate it.

Figure 2B:
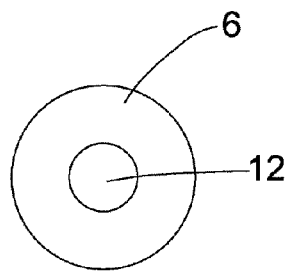
FIG. 2B shows a side view of a locking anchor disk.

FIG. 2B shows a top view of a locking anchor 6. In FIG. 2B, it is shown as a round disk; however, it can be any shape. It should be larger laterally than it is in thickness. The thickness of the anchor disk 6 and the separation of the serrations 8 should be chosen so that either one or preferably two serrations lock into the disk 6 at any time.

Figure 2C:
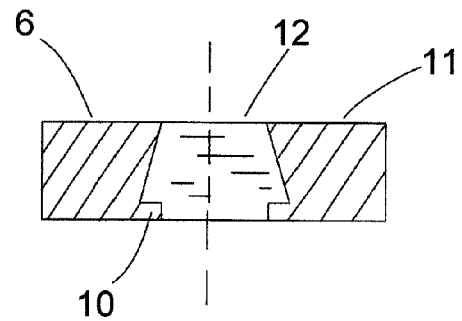
FIG. 2C shows a side sectional view of the locking disk of FIG. 2B.

FIG. 2C shows a sectional view of an embodiment of an anchor disk 6. In this embodiment, there is a lower engaging ridge 10 near the bottom of the center hole 12 that can engage the serrations 8 as well as the top of the disk 11. This allows a double grip top and bottom to prevent the disk from slipping off and to allow the device to handle a greater tension.

Figure 3:
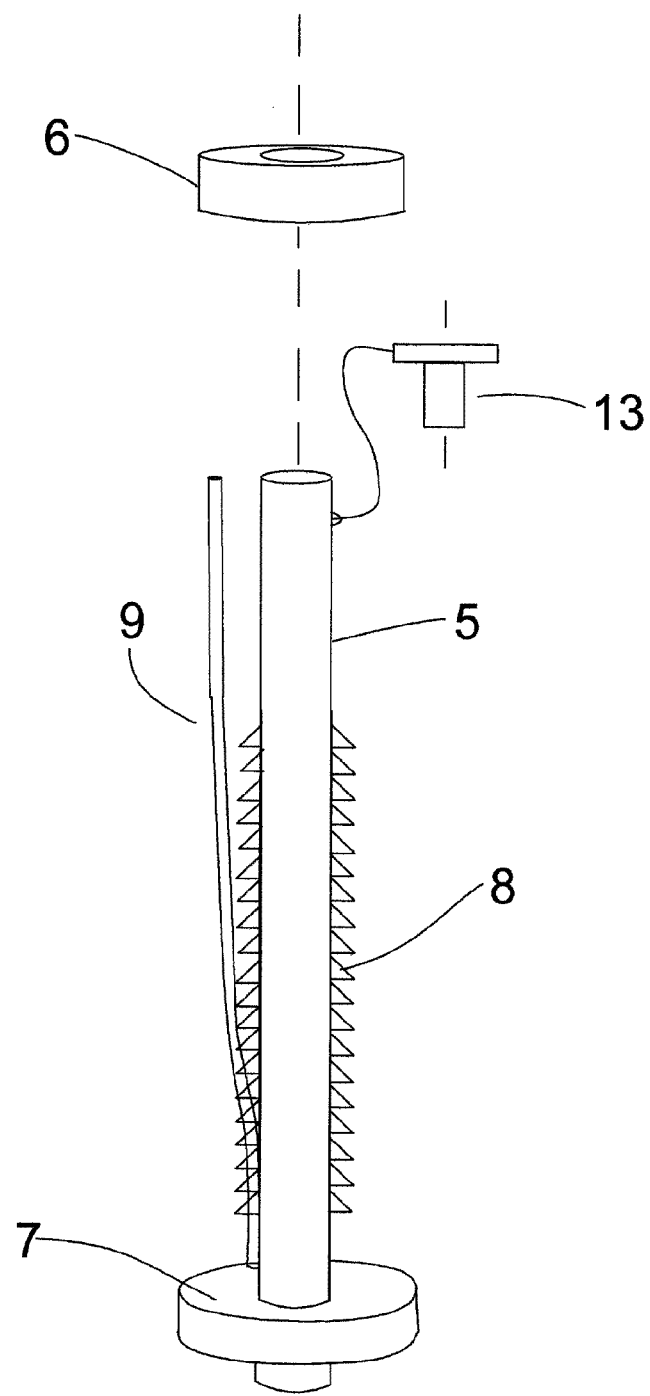
FIG. 3 shows a perspective view of an embodiment of the present invention usable for hemostasis.

FIG. 3 shows an embodiment of the present invention that is of the same general construction, but much larger diameter. This embodiment can act as a hemostasis device allowing the surgeon to repair a cut blood vessel, and then to continue to use the same hole for the rest of the surgery. The tube 5 can be supplied in several sizes of inside diameter 12 mm, 10 mm and 5 mm or other convenient sizes between around 5 mm up to around 15 mm. The length can be around 12 cm. The balloon 7 can be around 3 cm as well as the width of the anchor disk around 3 cm. The inflation tube 9 can have a diameter of around 3 mm. The balloon 7 can preferably be around 2 cm from the lower serration. An optional cap 13 with a top of around 13 mm can be adapted to fit into the open end of the stem tube 5.

Figure 4:
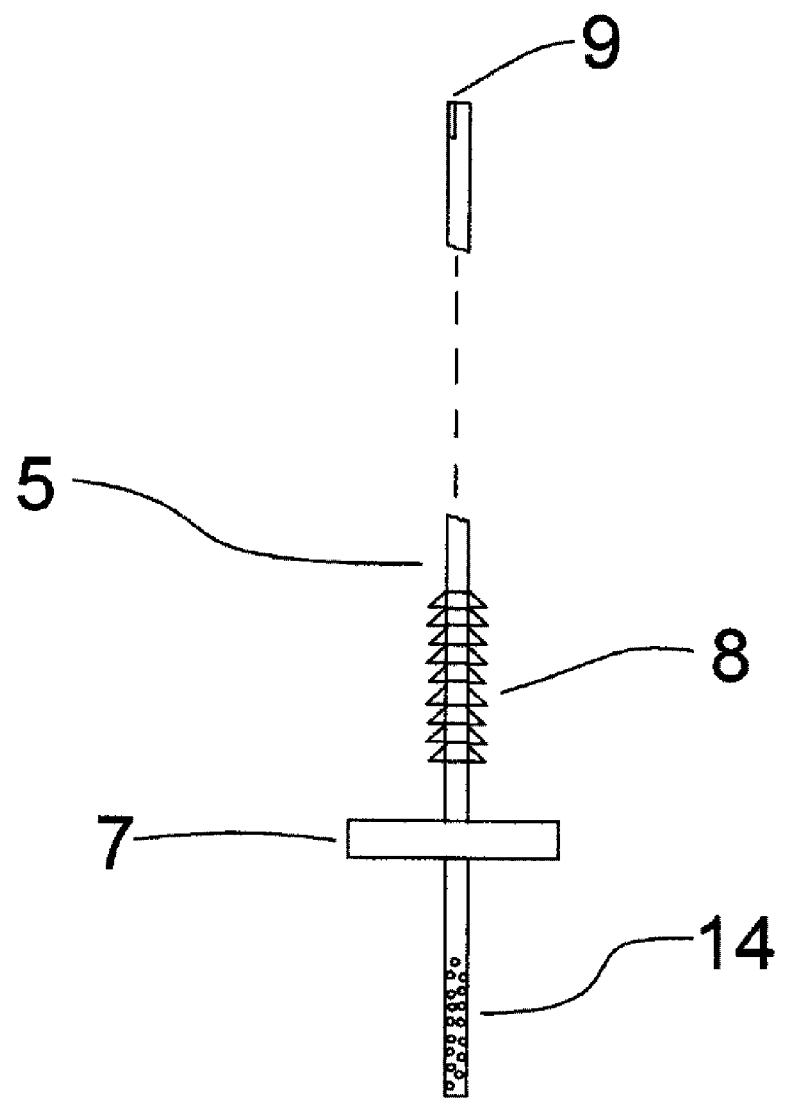
FIG. 4 shows a perspective view of an embodiment of the present invention usable as a drain.

FIG. 4 shows an embodiment of the invention that can be used as a surgical drain. The general construction is the same. The outside diameter can be around 5 mm or 10 mm. The stem 5 is hollow with optional holes 14 on the lower end. The inflation tube 9 can be located inside the hollow stem 5 (of course it could also run along side the stem 5). The elongated top of the stem can be attached to appropriate suction of draining apparatus known in the art.

Figure 5:
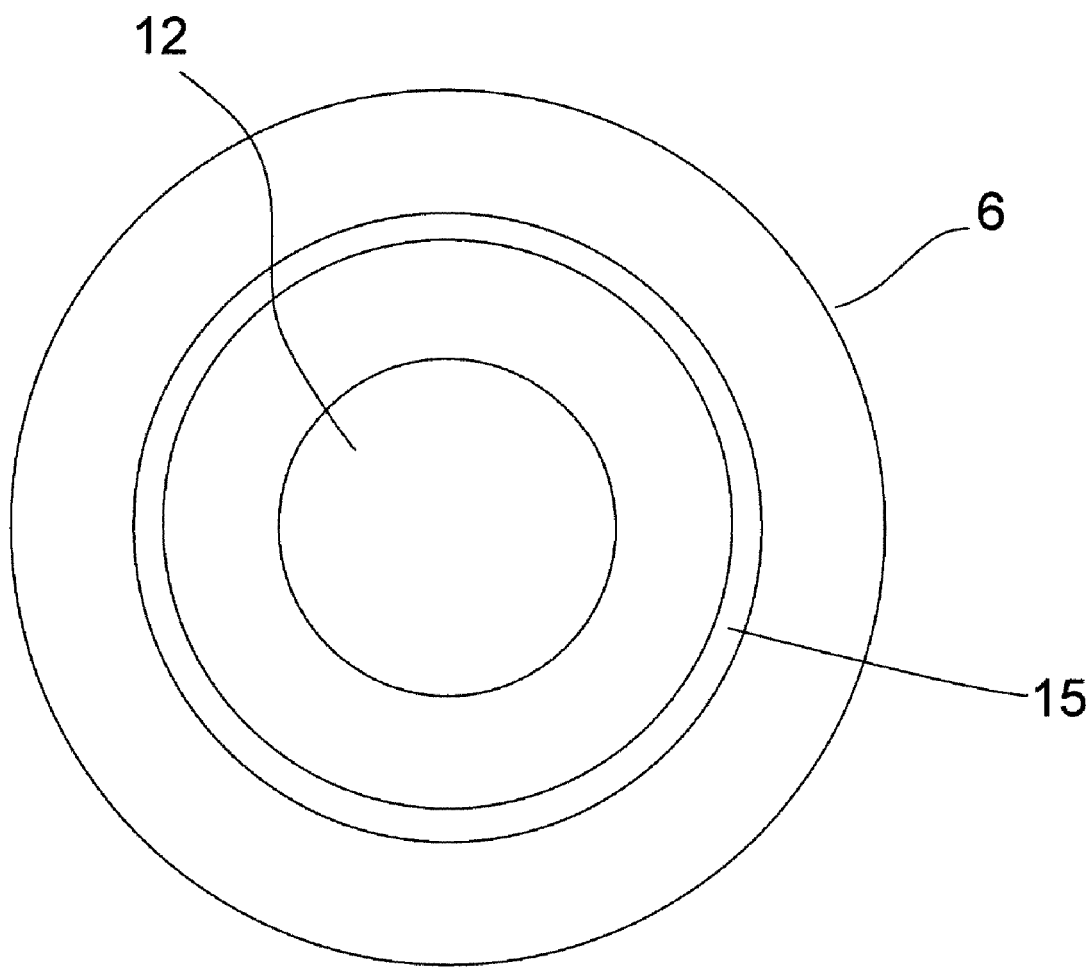
FIG. 5 shows a bottom view of a locking disk with a groove for containing a antiseptic.

FIG. 5 shows the bottom side of an embodiment of anchor disk. A groove 15 circles the disk 6 on the bottom surface. This groove 15 can contain an antibacterial or antiseptic paste of compound to help prevent infection.

The devices of the present invention can be made of any rigid or semi-rigid material with hard polymers being preferred. The devices can be supplied in sterile packages ready for use in surgery. The devices can also be supplied in various convenient lengths to match the required length needed for different patients.

The surgeon wishing to close an entrance hole merely inserts the balloon and lower stem of the embodiment of FIGS. 1-2 into the hole in the abdominal wall with the stem clamped or otherwise held below its top end (to prevent losing it in the hole). The surgeon can then insert the anchor cap on the top of the stem, clicking it down over the first serration. This will prevent the device from getting lost in the hole. Next, the balloon can be inflated using a small bulb or hand pump. The inflation tube can be pinched closed (or otherwise closed). Finally, using a tool or by hand, the surgeon can carefully advance the anchor cap downward along the serrations until the proper tension is made on the tissue for healing. Removing the device in about 5-6 days merely requires deflating the balloon through the inflation tube, and pulling the device out of the abdomen. The final, tiny diameter hole in the tissue immediately closes and heals.

In the case of the hemostasis device (FIG. 3). The insertion is very similar to the first case. The device can be quickly inserted into the hole, inflated, and locked down. The surgeon can then clamp off the blood vessel through the hollow stem of the device. Surgery can continue through the device. After the surgery is complete, the balloon can be deflated, and the device removed. A close device of the first embodiment can then be used as described above to close the hole for healing.

In the case of a drain, the third embodiment of the device (FIG. 4) can be inserted, inflated and anchored in the same manner. However, in this case, the top of the device can be connected to a suction of drainage apparatus in the usual way. After the drain is removed, a close device of the first embodiment (FIG. 1) can be used to close the hole.

Figure 6:
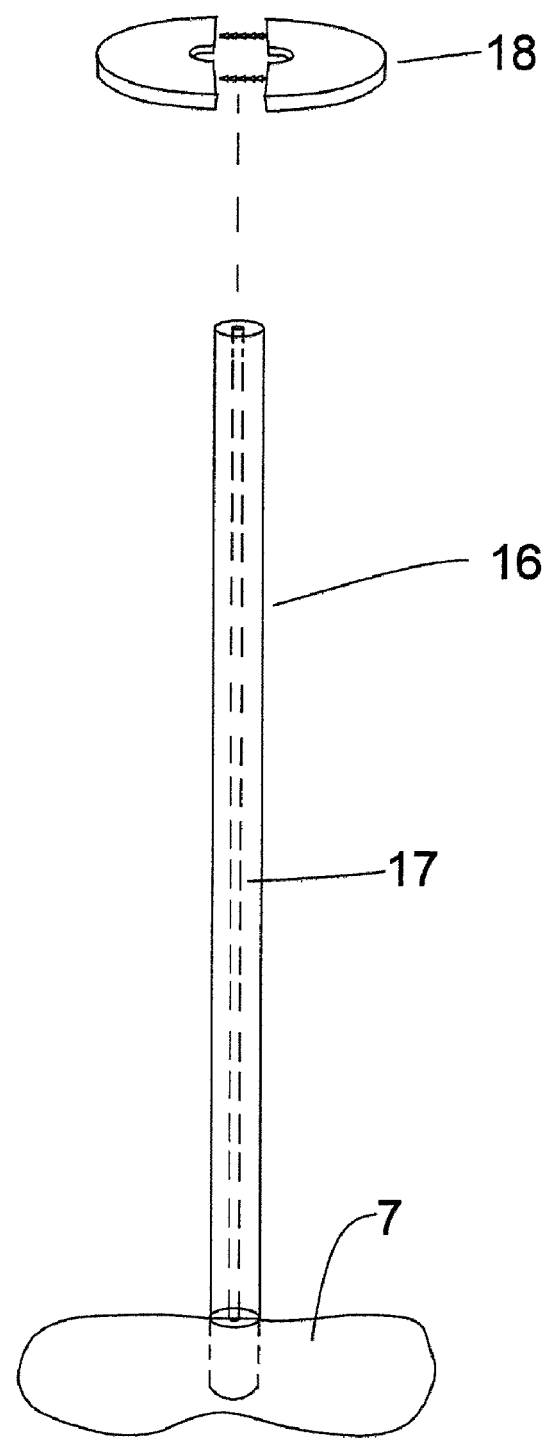
FIG. 6 shows an alternate embodiment which uses a soft tube as a stem and a split disk.

FIG. 6 shows an alternate embodiment of the present invention. A soft tube 16 can be used as stem. This tube can be around 2 mm in outer diameter in a preferred size. A split disk 18 can slip over the tube 16, move down to a tight position on the patient, and then be squeezed together to lock on the tube 17. The diameter of the inner hole of the split disk 18 can be just a small amount smaller than the outer diameter of the tube. For example, this hole could be 1.8 mm in a preferred size for use with a 2 mm tube. The inner channel 17 of the tube should not be pinched closed by the device. It can be used to inflate and deflate the balloon 7 as previously described or used in other ways previously described.

FIGS. 7A and 7B show a detail of an embodiment of a split disk 18. FIG. 7A shows the disk in the closed, or pinched, configuration, while FIG. 7B shows the disks in the open configuration. The two disk halves 19a and 19b can move together while a serrated pin 20 slides into a grooved channel 21. The piece clicks together to the required tightness.

Figure 8:
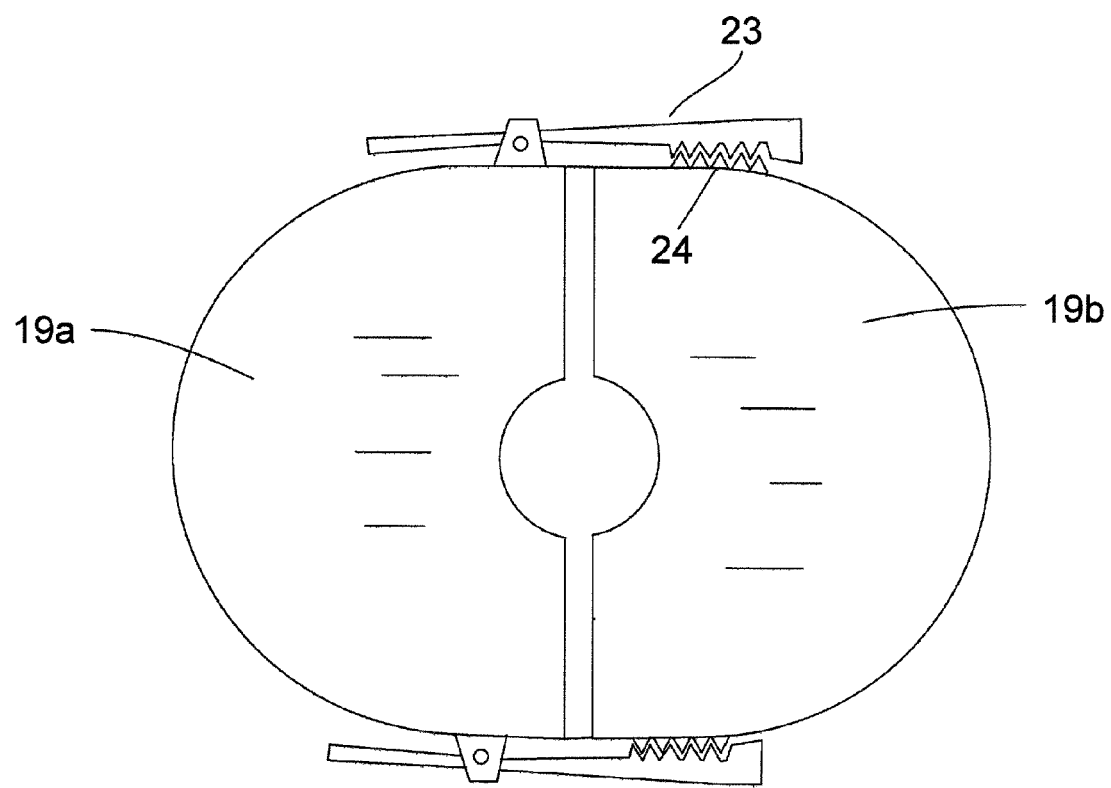
FIG. 8 shows another embodiment of a split disk.

FIG. 8 shows an alternate embodiment of a split disk. Here the halves can move apart and together along an open channel with a pin (not shown) while being gripped on the outside with an engagement 23 on the half disk 19a that engages teeth 24 on the other half disk 19b. This embodiment can be easily separated at any time by the doctor.

Several descriptions and illustrations have been presented to aid in understanding the present invention. One skilled in the art will realize that numerous changes and variations are possible without departing from the spirit of the invention. Each of these changes and variations is within the scope of the present invention.

I claim:

1. A laparoscopic surgical device adapted to be inserted into a laparoscopic port in a patient's abdomen comprising, in combination:
    an elongated stem having a proximal and distal end with a plurality of serrations along said stem, said serrations each having a flat bottom and inclined top;
    an inflatable balloon attached to said stem near its distal end, said balloon having an inflation tube running in or along said stem to near its proximal end, wherein said balloon can be inflated and deflated with said inflation tube;
    an anchor disk fitting over said stem, wherein said anchor disk can be slid downward over said serrations, but not upward;
    whereby, said balloon, when inflated, and said anchor disk pinch tissue of said entrance port for healing.

2. The laparoscopic surgical device of claim 1 wherein said stem has an outside diameter of between 2-5 mm.

3. The laparoscopic surgical device of claim 1 wherein said stem is hollow and has an inside diameter of between 5 mm and 15 mm, whereby, said device can be used as a hemostasis device.

4. The laparoscopic surgical device of claim 1 wherein said stem is hollow and has an outside diameter of between around 5 mm and 10 mm, wherein said inflation tube is inside said stem, and whereby said device can be used as a surgical drain.

5. The laparoscopic surgical device of claim 1 wherein said anchor disk has a top surface and bottom surface and center hole passing from said top surface through to said bottom surface with a protruding ridge located in said hole near said bottom surface, wherein, said top surface can grip a first serration on said stem, and said protruding ridge can grip a second serration on said stem.

6. The laparoscopic surgical device of claim 1 wherein said stem is between 2 and 5 mm outside diameter, said anchor disk is around 3 cm diameter, and said balloon is around 3 cm across when inflated.

7. A laparoscopic surgical device comprising an elongated stem with a distal and proximal end; an inflatable balloon near the distal end, and a sliding anchor disk on the proximal end, wherein said sliding anchor disk can slide down said stem to lock the device in place.

8. The laparoscopic surgical device of claim 7 wherein said stem has an outside diameter of between 2-5 mm.

9. The laparoscopic surgical device of claim 7 wherein said stem is hollow and has an inside diameter of between 5 mm and 15 mm, whereby, said device can be used as a hemostasis device.

10. The laparoscopic surgical device of claim 7 wherein said stem is hollow and has an outside diameter of between around 5 mm and 10 mm, wherein said inflation tube is inside said stem, and whereby said device can be used as a surgical drain.

11. The laparoscopic surgical device of claim 7 wherein said anchor disk is a split disk with a right half and a left half, and wherein the right half can engage the left half to hold said disk engaged on said stem by pinching said stem.

12. The laparoscopic surgical device of claim 7 wherein said stem is between 2 and 5 mm outside diameter, said anchor disk is around 3 cm diameter, and said balloon is around 3 cm across when inflated.

13. A laparoscopic surgical device adapted to be inserted into a laparoscopic port in a patient's abdomen comprising, in combination:
    an elongated stem having a proximal and distal end;
    an inflatable balloon attached to said stem near its distal end, said balloon having an inflation tube running in or along said stem to near its proximal end, wherein said balloon can be inflated and deflated with said inflation tube;
    an anchor disk fitting over said stem, wherein said anchor disk can be slid downward over said stem;
    wherein said anchor disk has a top surface and bottom surface and center hole passing from said top surface through to said bottom surface
    whereby, said balloon, when inflated, and said anchor disk pinch tissue of said entrance port for healing.

14. The laparoscopic surgical device of claim 13 wherein said stem has an outside diameter of between 2-5 mm.

15. The laparoscopic surgical device of claim 13 wherein said stem is hollow and has an inside diameter of between 5 mm and 15 mm, whereby, said device can be used as a hemostasis device.

16. The laparoscopic surgical device of claim 13 wherein said stem is hollow and has an outside diameter of between around 5 mm and 10 mm, wherein said inflation tube is inside said stem, and whereby said device can be used as a surgical drain.

17. The laparoscopic surgical device of claim 13 wherein said stem is between 2 and 5 mm outside diameter, said anchor disk is around 3 cm diameter, and said balloon is around 3 cm across when inflated.

18. The laparoscopic surgical device of claim 13 wherein said stem is a soft tube of outside diameter around 2 mm, and wherein said anchor is a split disk with a right half that engages a left half pinching said soft tube between the right half and left half.

19. The laparoscopic surgical device of claim 18 wherein said right half engages said left half with at least one serrated pin.

20. The laparoscopic surgical device of claim 18 wherein said right half and left half are held together by an engagement mechanism on one of said right or left halves having a first plurality of engaging teeth that engage a second plurality of teeth on the other of said right or left halves.

* * * * *